United States Patent
Katsuta et al.

(10) Patent No.: US 7,786,325 B2
(45) Date of Patent: Aug. 31, 2010

(54) PROCESS FOR PRODUCING O-METHYL-N-NITROISOUREA

(75) Inventors: Hiroyuki Katsuta, Chiba (JP); Kiyoshi Takahashi, Kuga-gun (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/278,498

(22) PCT Filed: Feb. 7, 2007

(86) PCT No.: PCT/JP2007/000067

§ 371 (c)(1),
(2), (4) Date: Aug. 6, 2008

(87) PCT Pub. No.: WO2007/091392

PCT Pub. Date: Aug. 16, 2007

(65) Prior Publication Data

US 2009/0036711 A1    Feb. 5, 2009

(30) Foreign Application Priority Data

Feb. 10, 2006    (JP) ............................. 2006-033942

(51) Int. Cl.
*C07C 275/68* (2006.01)
(52) U.S. Cl. ...................................................... 564/33
(58) Field of Classification Search ................... 564/33
See application file for complete search history.

(56) References Cited

U.S. PATENT DOCUMENTS

| | | | |
|---|---|---|---|
| 3,098,872 A | | 7/1963 | Weakley et al. |
| 3,799,988 A | * | 3/1974 | Hashimoto et al. .......... 564/157 |
| 5,051,434 A | | 9/1991 | Kozo et al. |
| 6,008,363 A | | 12/1999 | Uneme et al. |
| 6,124,466 A | | 9/2000 | Matsuno et al. |
| 6,265,582 B1 | | 7/2001 | Uneme et al. |
| 2009/0018363 A1 | | 1/2009 | Kamekawa et al. |
| 2009/0018364 A1 | | 1/2009 | Yamagata et al. |

FOREIGN PATENT DOCUMENTS

| | | |
|---|---|---|
| JP | 59-222451 A | 12/1984 |
| JP | 2-288860 A | 11/1990 |
| JP | 60-220019 A | 8/1994 |
| JP | 09-031030 A | 2/1997 |
| JP | 9-067342 A | 3/1997 |
| JP | 10-120666 A | 5/1998 |
| JP | 2000-103775 A | 4/2000 |
| JP | 2000-103776 A | 4/2000 |
| JP | 2003-516423 A | 5/2003 |
| JP | 2007-277232 A | 10/2007 |
| WO | WO 97/00867 A1 | 1/1997 |
| WO | WO 99/33809 A1 | 7/1999 |
| WO | WO 01/42787 A2 | 6/2001 |
| WO | WO 2007/105793 A1 | 9/2007 |

OTHER PUBLICATIONS

Form PCT/ISA/210 (International Search Report) dated Apr. 17, 2007.
N. Heyboer et al., "Note on the Conversion of the Amino Group of Amino Acids Into The Nitroguanidino Group", Recueil des Travaux Chimiques des Pays-Bas, 1962, vol. 81, pp. 69-72 (cited in the attached International Search Report and on p. 3 of the specification).
J. W. Janus, "O-Alkylation of Urea", Journal of the Chemical Society, Apr. 20, 1955, pp. 3551-3552 (cited on p. 3 of the specification).

* cited by examiner

*Primary Examiner*—Peter G. O'Sullivan
(74) *Attorney, Agent, or Firm*—Buchanan Ingersoll & Rooney PC

(57) ABSTRACT

Disclosed is an industrially advantageous process for producing O-methyl-N-nitroisourea. Disclosed is a process for obtaining O-methyl-N-nitroisourea represented by the following chemical formula (1) or a salt thereof in a high yield by performing the nitration of O-methylisourea represented by the following chemical formula (2) or a salt thereof with nitrating agents in the presence of fuming sulfuric acid.

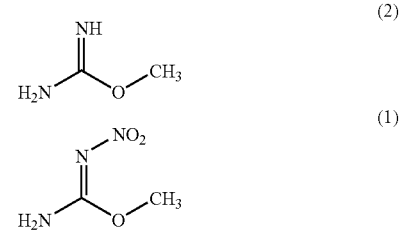

2 Claims, No Drawings

PROCESS FOR PRODUCING O-METHYL-N-NITROISOUREA

TECHNICAL FIELD

The present invention relates to an improved process for producing O-methyl-N-nitroisourea which is useful as a synthetic intermediate of an insecticide.

BACKGROUND ART

O-methyl-N-nitroisourea is represented by the following chemical formula (1).

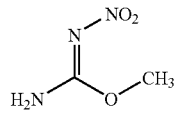
(1)

O-methyl-N-nitroisourea is useful, for example, as a synthetic intermediate of guanidine derivatives which are useful as an insecticide.

As a process for producing O-methyl-N-nitroisourea, there has been a known process for reacting O-methylisourea with nitrating agents.

In the process, after the nitration is performed with nitric acid in sulfuric acid, the reaction mixture is poured into cold water, or ice, or ice water, and cooled to about −15 degree centigrade. When the generated O-methyl-N-nitroisourea is collected by filtration, O-methyl-N-nitroisourea is obtained in only about 75% yield by filtration (for example, refer to Non-patent Document 1). Because O-methyl-N-nitroisourea is water soluble.

Furthermore, by extracting O-methyl-N-nitroisourea from a filtrate after filtration, the yield is increased to about 90%. However, since the solubility of O-methyl-N-nitroisourea to a solvent which can be used for extraction is not so high, large amount of organic solvent is needed for the extraction and the procedure becomes complicated. Thus, the process is not industrially advantageous (for example, refer to Patent Document 2, Non-patent Documents 1 and 2).

Further, since effective isolation and purification of N-nitroisourea are difficult, N-nitroisourea is used for the next reaction without isolation (refer to Patent Document 1).

Patent Document 1: WO01/42787
Patent Document 2: WO97/00867
Non-patent Document 1: Recueil des Travaux Chimiques des Pays-Bas, Vol. 81, p. 69 (1962)
Non-patent Document 2: Journal of Chemical Society, p. 3551 (1955)

DISCLOSURE OF THE INVENTION

An object of the present invention is to provide an industrially excellent process for producing O-methyl-N-nitroisourea which is an important intermediate for producing guanidine derivatives having an insecticidal activity, by overcoming the aforementioned problems in the prior art. That is, an object of the invention is to provide a process in which the reaction yield of O-methyl-N-nitroisourea obtained by nitration of O-methylisourea is enhanced and in which O-methyl-N-nitroisourea is easily isolated by an industrially available process.

In order to achieve the above objects, the present inventors have conducted an extensive study of a process for producing O-methyl-N-nitroisourea or a salt thereof. As a result, the present inventors have found that O-methyl-N-nitroisourea represented by the following chemical formula (1) or a salt thereof is obtained in a high yield by reacting O-methylisourea represented by the following chemical formula (2) or a salt thereof with nitrating agents in the presence of fuming sulfuric acid.

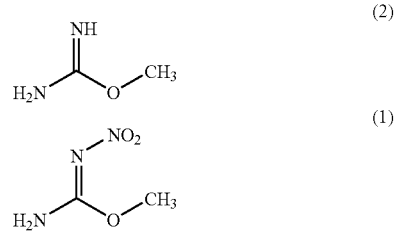

Even though it is supposed that there are by-products generated by nitration, starting material and large amount of sulfates and nitrates in the reaction mixture of the present invention, it is usually unexpected that the compound represented by the chemical formula (1) or a salt thereof is obtained in a high yield.

The present inventors have conducted a detailed study of the nitration of the compound represented by the chemical formula (2) with nitrating agents and as a result, have found that water generated during the reaction is very influential on the reaction, causing stoppage of the reaction and deterioration of the reaction yield.

That is, the nitration is a reversible reaction, and water generated the reaction reacts with O-methyl-N-nitroisourea to give O-methylisourea. For this reason, the reaction does not fully proceed and the reaction yield of O-methyl-N-nitroisourea becomes low. Furthermore, when large amount of sulfuric acid and nitric acid are used, the influence of by-produced water becomes small so that the reaction proceeds and the reaction yield is enhanced. However, since the crystallization yield is lowered, the isolation of O-methyl-N-nitroisourea becomes difficult to be performed and at the same time large amount of acidic waste is generated.

The present inventors have conducted an extensive study of the dehydrating conditions to enable an easy and an effective isolation process without influence of a sulfuric acid and nitrating agents such as nitric acid in the reaction mixture. As a result, the present inventors have further found an optimum condition of employing fuming sulfuric acid as a dehydrating agent in the reaction.

In the present invention, by removal of a part of water or whole water generated in the reaction using fuming sulfuric acid, the reaction yield is greatly enhanced. Furthermore, using this reaction condition, the efficiency of workup procedure can be greatly improved, while O-methyl-N-nitroisourea can be obtained in a high yield by simple isolation process.

As described above, a process for producing O-methyl-N-nitroisourea of the present invention has been completed.

That is, the present invention relates to a process for producing O-methyl-N-nitroisourea represented by the following chemical formula (1) or a salt thereof, in which the nitration of O-methylisourea represented by the following chemical formula (2) or a salt thereof is performed with nitrating agents in the presence of fuming sulfuric acid, (2)

[Structure: H2N-C(=NH)-O-CH3]

(1)

[Structure: H2N-C(=N-NO2)-O-CH3]

According to the present invention, the reaction yield of O-methyl-N-nitroisourea is easily enhanced and O-methyl-N-nitroisourea is easily isolated by an industrially available process. In other words, according to the present invention, O-methyl-N-nitroisourea of the chemical formula (1) which is a necessary intermediate for producing nitroguanidine derivatives having an insecticidal activity can be cheaply and easily produced.

BEST MODE FOR CARRYING OUT THE INVENTION

The production process of the present invention can be performed, for example, in accordance with the reaction condition as described below. According to the following production process, when a product is obtained as an isolated compound, the obtained compound can be converted into a salt, or when a product is obtained in the form of a salt, the obtained product can be converted into an isolated compound respectively according to a usual process. Also, similarly, when a starting material can be a salt, it can be used not only as an isolated compound but also as a salt. Accordingly, the starting material to be used for the following production process and its reaction product also include a salt thereof.

The acid forming salt with O-methyl-N-nitroisourea represented by the above chemical formula (1), O-methylisourea represented by the above chemical formula (2) may be allowable acids in terms of organic chemistry. Examples thereof include inorganic acids such as hydrochloric acid, hydrobromic acid, hydroiodic acid, phosphoric acid, sulfuric acid, perchloric acid and the like; and organic acids such as formic acid, acetic acid, tartaric acid, malic acid, citric acid, oxalic acid, succinic acid, benzoic acid, picric acid, methanesulfonic acid, p-toluenesulfonic acid and the like. Of these acids, preferably used are hydrochloric acid and sulfuric acid. As a salt of O-methylisourea, particularly preferably used are sulfate, ½ sulfate and monomethyl sulfate.

By performing the nitration of the compound represented by the chemical formula (2) or a salt thereof with nitrating agents in the presence of fuming sulfuric acid, O-methyl-N-nitroisourea represented by the chemical formula (1) or a salt thereof can be obtained (following reaction formula). After completion of the reaction, the reaction mixture is diluted with water in a proper amount and the precipitate is filtrated. Thus, the compound represented by the chemical formula (1) or a salt thereof can be easily isolated.

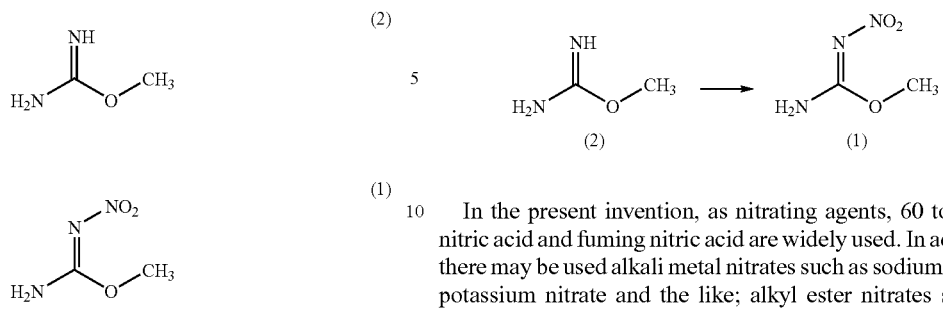

In the present invention, as nitrating agents, 60 to 100% nitric acid and fuming nitric acid are widely used. In addition, there may be used alkali metal nitrates such as sodium nitrate, potassium nitrate and the like; alkyl ester nitrates such as ethyl nitrate, amyl nitrate and the like; nitronium tetrafluoroborate, nitronium trifluoromethanesulfonate, and the like. Particularly preferably used are nitric acid and fuming nitric acid.

The nitrating agents can be used in an amount of from about 1.0 to 20 moles, based on 1 mole of the compound represented by the chemical formula (2) or a salt thereof, but preferably in an amount of from about 1.5 to 10 moles when nitric acid is used. Furthermore, when fuming nitric acid is used, it is preferably used in an amount of from about 1.0 to 3.0 moles.

In the reaction according to the present invention, when fuming sulfuric acid is used as a dehydrating agent, the reaction yield is enhanced.

As the fuming sulfuric acid, fuming sulfuric acid with 5 to 50 weight % of sulfur trioxide contained therein can be used. However, fuming sulfuric acid of 20 to 30 weight % is preferable.

The fuming sulfuric acid can be used in an amount of from 0.5 to 50 times of starting material on the basis of the weight of the starting material, but particularly preferably in an amount of from 0.5 to 10 times. Furthermore, it may be used as a solvent.

The reaction may be carried out without using any solvent. However, the reaction is usually carried out in the presence of an acidic solvent such as sulfuric acid, acetic acid, acetic anhydride, trifluoroacetic anhydride, trifluoromethanesulfonic acid or the like. As desired, a solvent which does not adversely affect the reaction or a mixture thereof may be used. In addition to the above acidic solvents, aromatic hydrocarbons such as chlorobenzene, dichlorobenzene and the like; halogenated hydrocarbons such as dichloromethane, chloroform, 1,2-dichloroethane, carbon tetrachloride and the like; saturated hydrocarbons such as hexane, heptane, cyclohexane and the like; ethers such as diethyl ether, tetrahydrofuran, dioxane and the like; ketones such as acetone, methylethyl ketone and the like; sulfoxides such as dimethyl sulfoxide and the like; and alcohols such as methanol, ethanol, propanol, isopropanol and the like may be used as solvent. These solvents can be used singly, or two or more kinds may be used in combination in a proper ratio, for example, in a ratio of about 1:1 to 1:10 (volume ratio). When the reaction mixture is not homogeneous, the reaction may be carried out in the presence of a phase transfer catalyst such as quaternary ammonium salt such as triethylbenzylammonium chloride, tri-n-octylmethylammonium chloride, trimethyldecylammonium chloride, tetramethylammonium bromide, cetylpyridinium bromide and the like, crown ethers or the like. As a solvent, particularly preferably used is sulfuric acid.

The reaction temperature in the nitration according to the present invention is usually in the range of about −50 to 100 degree centigrade and preferably in the range of about −20 to 30 degree centigrade. The reaction time is in the range of about 10 minutes to 24 hours and preferably in the range of about 2 to 10 hours.

After completion of the reaction, the reaction mixture is diluted with water, or ice, or ice water so that a mixture containing O-methyl-N-nitroisourea represented by the chemical formula (1) or a salt thereof can be obtained. Specifically, after completion of the reaction, the reaction mixture is poured into cold water, or ice, or ice water, and then the precipitate is filtrated. Thus, a mixture containing O-methyl-N-nitroisourea represented by the chemical formula (1) or a salt thereof can be isolated. The reaction mixture can be filtered before dilution if necessary.

The amount of water to be used for diluting the reaction mixture is from 1.0 to 5.0 times and preferably from 2.0 to 3.0 times on the basis of the weight, of sulfuric acid present in the reaction mixture.

EXAMPLES

The present invention is now illustrated in detail below with reference to Examples. However, the present invention shall not be limited in any way by these Examples.

Example 1

O-methylisourea.½ sulfuric acid (100 g) were introduced into fuming sulfuric acid (100 g) which was cooled to −10 degree centigrade while maintaining a temperature at not more than 0 degree centigrade. Next, mixed acid (a mixture of 150 g of sulfuric acid and 60 g of fuming nitric acid having a specific gravity of 1.52) was added dropwise to the reaction mixture while maintaining a temperature at −10 to 0 degree centigrade. Thereafter, the reaction mixture was stirred at −5 degree centigrade for 24 hours. The reaction yield was analyzed by high performance liquid chromatography and as a result, 97% of the reaction yield was obtained.

The aforementioned reaction mixture was added dropwise to water (685 g) while maintaining a temperature at not more than 2 degree centigrade. The mixture was stirred at −10 degree centigrade for 3 hours, and then the precipitate was filtrated to obtain a desired O-methyl-N-nitroisourea (quantity: 86.3 g, purity: 94%, yield: 84%).

$^1$H-NMR (DMSO, ppm): 3.70 (3H, S), 8.90 (2H, br)

Comparative Example 1

O-methylisourea.½ sulfuric acid (20 g) were introduced into sulfuric acid (20 g) at a temperature of from 15 to 20 degree centigrade. Next, mixed acid (a mixture of 30 g of sulfuric acid and 12 g of fuming nitric acid having a specific gravity of 1.52) was added dropwise to the reaction mixture at the same temperature. Thereafter, the reaction mixture was stirred at 20 degree centigrade for 24 hours. The reaction yield was analyzed by high performance liquid chromatography and as a result, 82% of the reaction yield was obtained.

The aforementioned reaction mixture was added dropwise to 196 g of water at 0 degree centigrade while maintaining the temperature. The same mixture was stirred at 0 degree centigrade for 1 hour, and then a 20% aqueous sodium hydroxide solution (75 g) was added dropwise thereto while maintaining the same temperature. Further, the reaction mixture was stirred for 1 hour, and then the precipitate was filtrated to obtain a desired O-methyl-N-nitroisourea (quantity: 9.5 g, purity: 90%, yield: 44%).

Comparative Example 2

The reaction was carried out in the same manner as in Example 1, except that anhydrous sodium sulfate was used instead of fuming sulfuric acid. As a result, the reaction yield was about 80% and the improvement of the reaction yield was not recognized.

The invention claimed is:

1. A process for producing O-methyl-N-nitroisourea represented by the following chemical formula (1) or a salt thereof, in which the nitration of O-methylisourea represented by the following chemical formula (2) or a salt thereof is performed with nitrating agents in the presence of fuming sulfuric acid

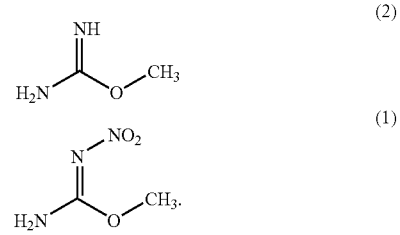

2. The process for producing O-methyl-N-nitroisourea as set forth in claim 1, in which said nitrating agents are nitric acid or fuming nitric acid.

* * * * *